(12) United States Patent
Suehira et al.

(10) Patent No.: US 9,429,414 B2
(45) Date of Patent: Aug. 30, 2016

(54) IMAGE PICKUP APPARATUS AND IMAGE PICKUP METHOD USING OPTICAL COHERENCE TOMOGRAPHY

(75) Inventors: Nobuhito Suehira, Kawasaki (JP); Kazuro Yamada, Kawasaki (JP); Norihiko Utsunomiya, Machida (JP); Takashi Naba, Kawasaki (JP); Ryoji Kurosaka, Tokyo (JP); Kei Suzuki, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 329 days.

(21) Appl. No.: 13/377,369

(22) PCT Filed: Jun. 15, 2010

(86) PCT No.: PCT/JP2010/003977
§ 371 (c)(1),
(2), (4) Date: Dec. 9, 2011

(87) PCT Pub. No.: WO2010/150483
PCT Pub. Date: Dec. 29, 2010

(65) Prior Publication Data
US 2012/0092677 A1    Apr. 19, 2012

(30) Foreign Application Priority Data

Jun. 25, 2009  (JP) ................. 2009-151484
Mar. 17, 2010  (JP) ................. 2010-061054

(51) Int. Cl.
*G01B 11/02*  (2006.01)
*G01B 9/02*   (2006.01)
*A61B 3/10*   (2006.01)

(52) U.S. Cl.
CPC ........... *G01B 9/02058* (2013.01); *A61B 3/102* (2013.01); *G01B 9/02012* (2013.01); *G01B 9/02072* (2013.04); *G01B 9/02091* (2013.01)

(58) Field of Classification Search
USPC ................................... 356/479, 497
See application file for complete search history.

(56) References Cited

U.S. PATENT DOCUMENTS

| | | | | |
|---|---|---|---|---|
| 5,268,741 A * | 12/1993 | Chou et al. | ................... | 356/479 |
| 6,160,826 A * | 12/2000 | Swanson et al. | ............... | 372/20 |
| 6,552,798 B2 * | 4/2003 | Ina et al. | ....................... | 356/493 |
| 7,382,470 B2 * | 6/2008 | Lindner et al. | ............... | 356/511 |
| 8,040,524 B2 * | 10/2011 | Ozawa | ........................ | 356/479 |

(Continued)

FOREIGN PATENT DOCUMENTS

| CN | 101229053 A | 7/2008 |
|---|---|---|
| CN | 101405562 A | 4/2009 |

(Continued)

*Primary Examiner* — Kara E Geisel
*Assistant Examiner* — Jonathon Cook
(74) *Attorney, Agent, or Firm* — Canon USA Inc. IP Division

(57) ABSTRACT

The present invention relates to an apparatus having a simple configuration capable of correctly detecting malfunction of an OCT apparatus by detecting the states of a light source and a sensor.

An image pickup apparatus includes a switching unit that switches between a first mode in which a combined light beam of a return light beam from a specimen and a reference light beam is detectable by a detecting unit and a second mode in which the reference light beam is detectable by the detecting unit.

The image pickup apparatus is switchable to the first mode on the basis of an intensity of the reference light beam detected by the detecting unit in the second mode.

13 Claims, 8 Drawing Sheets

(56) References Cited

U.S. PATENT DOCUMENTS

| | | | |
|---|---|---|---|
| 8,055,107 B2* | 11/2011 | Masuda | 385/26 |
| 2005/0140981 A1* | 6/2005 | Waelti | 356/479 |
| 2006/0126077 A1* | 6/2006 | Ueki et al. | 356/512 |
| 2006/0266109 A1* | 11/2006 | DiFoggio | 73/152.55 |
| 2007/0077045 A1* | 4/2007 | Kato | 396/17 |
| 2007/0127033 A1* | 6/2007 | Ueno | 356/497 |
| 2008/0079945 A1* | 4/2008 | Flowers et al. | 356/450 |
| 2008/0175465 A1* | 7/2008 | Jiang et al. | 382/131 |
| 2009/0027685 A1 | 1/2009 | Abe et al. | |
| 2009/0033870 A1 | 2/2009 | Hangai et al. | |
| 2009/0073455 A1* | 3/2009 | Onimura | 356/479 |
| 2009/0285354 A1* | 11/2009 | Hirose et al. | 378/19 |
| 2010/0033730 A1* | 2/2010 | Kim | 356/479 |
| 2010/0302550 A1* | 12/2010 | Hacker et al. | 356/479 |
| 2010/0315649 A1* | 12/2010 | Yamakita | 356/497 |

FOREIGN PATENT DOCUMENTS

| | | |
|---|---|---|
| EP | 1950526 A1 | 7/2008 |
| EP | 2022391 A1 | 2/2009 |
| EP | 2062526 A1 | 5/2009 |
| JP | H03-088504 | 9/1991 |
| JP | 2001-017459 | 1/2001 |
| JP | 2009-042197 A | 2/2009 |
| JP | 2009-066014 A | 4/2009 |
| JP | 2010-243280 A | 10/2010 |
| WO | 2005/122872 A2 | 12/2005 |
| WO | 2007/084750 A2 | 7/2007 |
| WO | 2007/133961 A2 | 11/2007 |
| WO | 2009/033111 A2 | 3/2009 |
| WO | 2009/136659 A1 | 11/2009 |
| WO | 2010/005091 A1 | 1/2010 |

* cited by examiner

IMAGE PICKUP APPARATUS AND IMAGE PICKUP METHOD USING OPTICAL COHERENCE TOMOGRAPHY

TECHNICAL FIELD

The present invention relates to an image pickup apparatus and an image pickup method using optical coherence tomography and, in particular, to an image pickup apparatus and an image pickup method using optical coherence tomography and used for examining the eye fundus or the skin.

BACKGROUND ART

In these days, image pickup apparatuses using optical coherence tomography (hereinafter referred to as "OCT apparatuses") are in practical use. Optical coherence tomography is an interferometric technique using low coherence light. Since OCT apparatuses can obtain a tomographic image with a resolution level that is substantially the same as the wavelength of light made incident on a specimen, the OCT apparatuses can capture a tomographic image with a high resolution.

For example, an OCT apparatus including a probe that repeatedly emits and receives a light beam is described in PTL 1. PTL 1 also describes the following problem. That is, even when the intensity of an output measurement light beam is within the range that does not damage a body tissue, the body tissue may be somewhat affected by the light beam if the light beam is continuously emitted to the tissue.

To solve this problem, the OCT apparatus controls a blocking unit that blocks a light beam transmitted to a probe in accordance with whether the probe is connected to the apparatus. Thus, if the probe is not connected to the apparatus, a light beam emitted to the outside of the apparatus can be blocked. Accordingly, the above-described negative impact on the human body can be prevented.

CITATION LIST

Patent Literature

PTL 1: Japanese Patent Laid-Open No. 2009-66014

SUMMARY OF INVENTION

As described above, medical apparatuses need to detect the state of a light beam emitted to the outside of an OCT apparatus from a clinical diagnosis point of view.

However, medical apparatuses also need to detect the state of the OCT apparatus and, in particular, detect the state of a measurement light beam and detect whether the OCT apparatus malfunctions.

Accordingly, the present invention provides a device capable of correctly detecting the state of an OCT apparatus in a simple manner.

According to an embodiment of the present invention, an image pickup apparatus for capturing an image of a specimen using optical coherence tomography is provided. The image pickup apparatus includes a light source configured to generate a light beam, a separating unit configured to separate the light beam emitted from the light source into a measurement light beam and a reference light beam, a detecting unit configured to detect a combined light beam of a return light beam from the specimen and the reference light beam, and a switching unit configured to switch between a first mode in which the combined light beam is detectable by the detecting unit and a second mode in which the reference light beam is detectable by the detecting unit.

The image pickup apparatus is switchable to the first mode on the basis of an intensity of the reference light beam detected by the detecting unit in the second mode.

According to another embodiment of the present invention, an image pickup apparatus for capturing an image of a specimen using optical coherence tomography is provided. The image pickup apparatus includes a light source configured to generate a light beam, a separating unit configured to separate the light beam emitted from the light source into a measurement light beam and a reference light beam, and a detecting unit configured to detect the reference light beam. The measurement light beam is led to the specimen on the basis of the intensity of the reference light beam detected by the detecting unit.

According to still another embodiment of the present invention, an image pickup apparatus for capturing an image of a specimen using optical coherence tomography is provided. The image pickup apparatus includes a light source configured to generate a light beam, a separating unit configured to separate the light beam emitted from the light source into a measurement light beam and a reference light beam, and a light intensity detection light detecting unit configured to detect a light intensity detection light beam obtained by separating the reference light beam. The measurement light beam is led to the specimen on the basis of the intensity of the light intensity detection light beam detected by light intensity detection light detecting unit, or an intensity of the measurement light beam led to the specimen is reduced.

According to yet still another embodiment of the present invention, an image pickup apparatus for capturing an image of a specimen using optical coherence tomography is provided. The image pickup apparatus includes a light source configured to generate a light beam, a separating unit configured to separate the light beam emitted from the light source into a measurement light beam and a reference light beam, a wavelength selection reflecting unit configured to receive an inspection light beam obtained by separating the measurement light beam, and a detecting unit configured to detect a combined light beam of a return inspection light beam from the wavelength selection reflecting unit and the reference light beam.

According to yet still another embodiment of the present invention, an image pickup method for capturing an image of a specimen using optical coherence tomography is provided. The method includes the steps of generating a light beam, separating the generated light beam into a measurement light beam and a reference light beam, detecting the reference light beam, and leading the measurement light beam onto the specimen on the basis of an intensity of the detected reference light beam.

According to yet still another embodiment of the present invention, an image pickup method for capturing an image of a specimen using optical coherence tomography is provided. The method includes the steps of generating a light beam, separating the generated light beam into a measurement light beam and a reference light beam, detecting a light intensity detection light beam obtained by separating the reference light beam, and one of leading the measurement light beam to the specimen on the basis of the intensity of the detected light intensity detection light beam and reducing an intensity of the measurement light beam led to the specimen.

According to the present invention, the state of an OCT apparatus can be correctly detected using a simple configuration.

Further features of the present invention will become apparent from the following description of exemplary embodiments with reference to the attached drawings.

DESCRIPTION OF EMBODIMENTS

Figure 1:
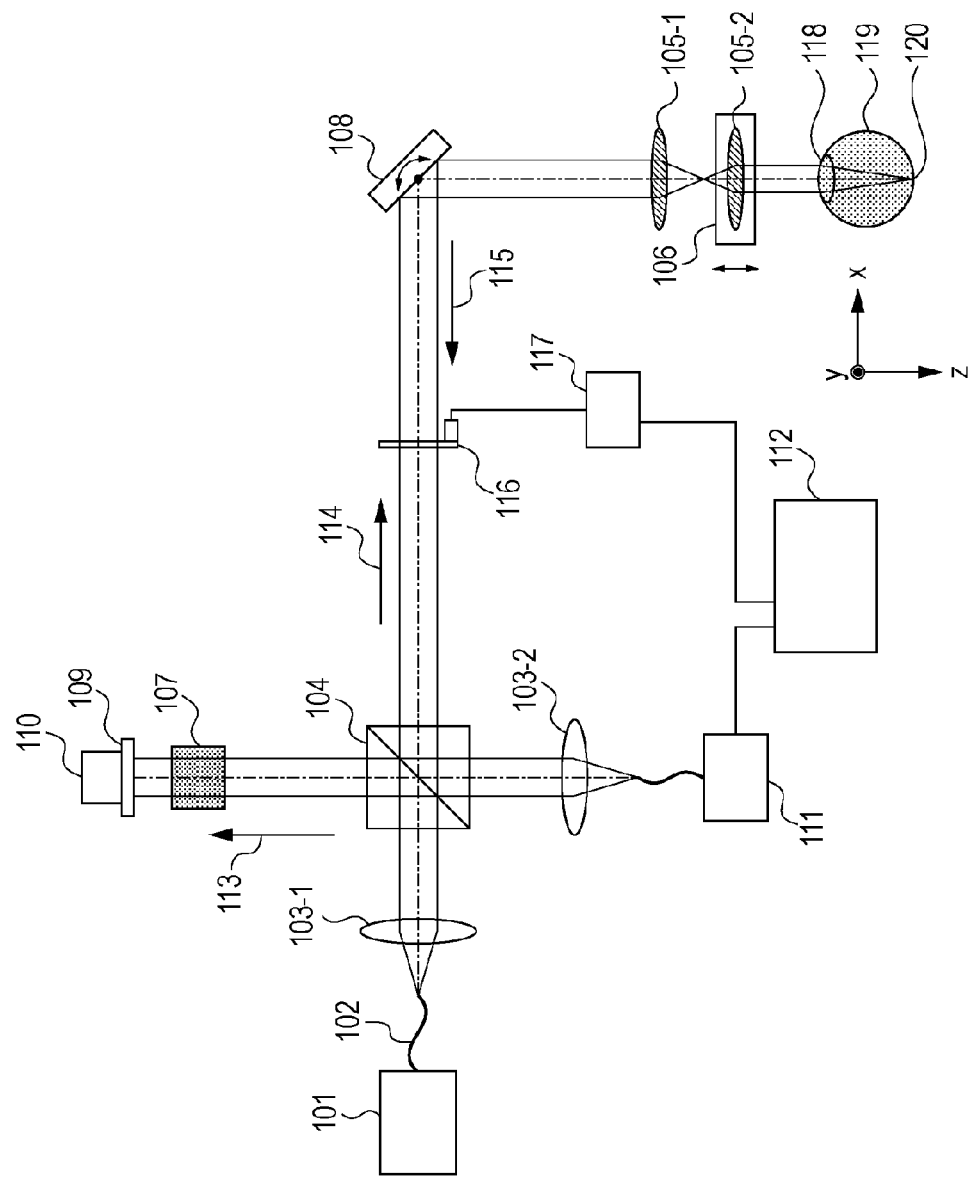
FIG. 1 is a diagram illustrating an optical system of an image pickup apparatus according to a first embodiment of the present invention.

According to embodiments of the present invention, an image pickup apparatus that uses optical coherence tomography (hereinafter also referred to as an "image pickup apparatus for capturing an image of a specimen using optical coherence tomography) is described with reference to FIG. 1. Note that in FIG. 1, the structure of a Michelson interferometer is shown. However, the present invention is applicable to the structure of a Mach-Zehnder interferometer shown in FIG. 5. In addition, the present invention is applicable to the structure of a multi-beam optical system shown in FIG. 6A.

Configuration of Image Pickup Apparatus

A light source 101 generates light (low coherence light). A super luminescent diode (SLD) can be used as the light source 101. Alternatively, an amplified spontaneous emission (ASE) can be used as the light source 101. Still alternatively, an ultra-short pulse laser, such as a titanium-sapphire laser, can be used as the light source 101. In this way, any light source that generates low coherence light can be used as the light source 101. In addition, the wavelength of light emitted from the light source 101 is not limited to any particular value. However, the wavelength of light is in the range of 400 nm to 2 mm. Note that as the range of the wavelength increases, the vertical resolution is more improved. In general, when the center wavelength is 850 nm, the resolution in the air is 6 mm in the range of 50 nm. The resolution in the air is 3 mm in the range of 100 nm.

A separating unit 104 separates the light emitted from the light source 101 into a measurement light beam 114 and a reference light beam 113. For example, a beam splitter or a fiber coupler can be used as the separating unit 104. In this way, any device that separates light can be used as the separating unit 104. In addition, the separation ratio can be optimally determined for the separating unit 104 in accordance with the specimen.

A detection unit 111 detects a combined light beam of a return light beam 115 from the specimen (an eye 119 of a person being tested) and the reference light beam 113. When a spectral domain OCT (SD-OCT) (post-spectroscopy system) is employed, the detection unit 111 (a spectrometer) includes a spectroscopic component for separating the combined light beam. At that time, for example, a diffraction grating or a prism can be used as the spectroscopic component. That is, any device that separates a light beam can be used as the spectroscopic component. The detection unit 111 further includes a sensor for detecting a light beam that is separated by the spectroscopic component. For example, a line sensor or a two-dimensional sensor can be used as the sensor. Any device that detects light can be used as the sensor.

In contrast, when a source swept-OCT (SS-OCT) (a pre-spectroscopy system), which is one of FD-OCTs, is employed, a light source that generates light beams having different wavelengths at different points of time is used. Accordingly, combined light beams of any of the generated light beams can be detected using a sensor, such as a photodiode. At that time, the above-described spectroscopic component is not needed in order to acquire spectrum information. Alternatively, when a time domain OCT (TD-OCT), which is different from FD-OCT, is employed, the detection unit 111 can be formed from a sensor, as in the SS-OCT.

According to the present embodiment, the image pickup apparatus further includes a switching unit 116 that switches between a first mode in which the return light beam 115 is combined as described above (i.e., a mode in which the return light beam 115 is led to the separating unit 104) and a second mode which is different from the first mode. That is, the switching unit 116 can switch between the first mode in which the combined light beam can be detected using the detection unit 111 and a second mode in which the reference light beam 113 can be detected using the detection unit 111.

In addition, according to the present embodiment, the image pickup apparatus can lead the measurement light beam 114 to the specimen 119 on the basis of the intensity of the reference light beam 113 detected by the detection unit 111.

For example, a switching unit 116 can block the optical path of the measurement light beam 114. At that time, the second mode represents a block mode. Furthermore, it is desirable that the switching unit 116 be configured so as to be able to control the transmission ratio of the measurement light beam 114. In such a case, a shutter described below can be used as the switching unit 116. That is, the switching unit 116 is configured so as to be able to change the intensity of the measurement light beam 114 that is led to the specimen 119.

Still furthermore, the switching unit 116 may include a reflecting member, such as a mirror, for reflecting the measurement light beam 114. At that time, it is desirable that the second mode be switched to the first mode on the basis of the reference light beam 113 detected by the detection unit 111 and the reflected measurement light in the second mode. In addition, when the transmission ratio is controlled, a rotary shutter having a circular hole can be used. At that time, it is desirable that a filter selected on the basis of the transmission ratio be mounted in the circular hole.

Yet still furthermore, the switching unit 116 may be configured so as to be able to change the optical path of the measurement light beam 114. At that time, the second mode represents the changed mode. In such a case, for example, a scanning optical unit (e.g., an XY scanner 108) for scanning the measurement light beam 114 over the specimen 119 can be used as the switching unit 116. However, any device that changes the optical path can be used.

Thus, according to the present embodiment, the image pickup apparatus can switch between the first mode and the second mode. Alternatively, it is desirable that the image pickup apparatus include a control unit 117 for controlling the switching unit 116 that switches between the first mode and the second mode. At that time, the control unit 117 switches the second mode to the first mode in accordance with the intensity of the reference light beam 113 detected by the detection unit 111 in the second mode. Alternatively, the control unit 117 may switch the first mode to the second mode in accordance with the intensity of the combined light beam detected by the detection unit 111 in the first mode. That is, the control unit 117 is configured so as to be able to reduce the intensity of the measurement light beam 114 led to the specimen 119. As used herein, the term "reducing the intensity of a light beam" refers to blocking a light beam as described above or decreasing the transmission ratio.

In this way, the intensity of the reference light beam 113 detected by the detection unit 111 can be detected. Accordingly, the state of the light source 101 and the state of the sensor can be detected. As a result, malfunction of the apparatus can be correctly detected using a simple configuration.

At that time, it is desirable that a comparing unit be provided for comparing the intensity of the reference light beam 113 detected by the detection unit 111 with a predetermined setting value (described in more detail below with reference to step A5 shown in FIG. 2). By using a value for determining whether malfunction occurs as the setting value (a reference value), the occurrence of malfunction of the apparatus can be detected.

If, at that time, the intensity of the light beam is within the range of the setting value, it is desirable that the second mode be changed to the first mode. In addition, if the intensity of the light beam is outside the range of the setting value, it is desirable that the second mode remains unchanged. This is because if the intensity of the reference light beam 113 is higher than the setting value, the intensity of the light beam higher than a required intensity may be emitted to the outside of the apparatus.

Image Pickup Method 1

Figure 2:
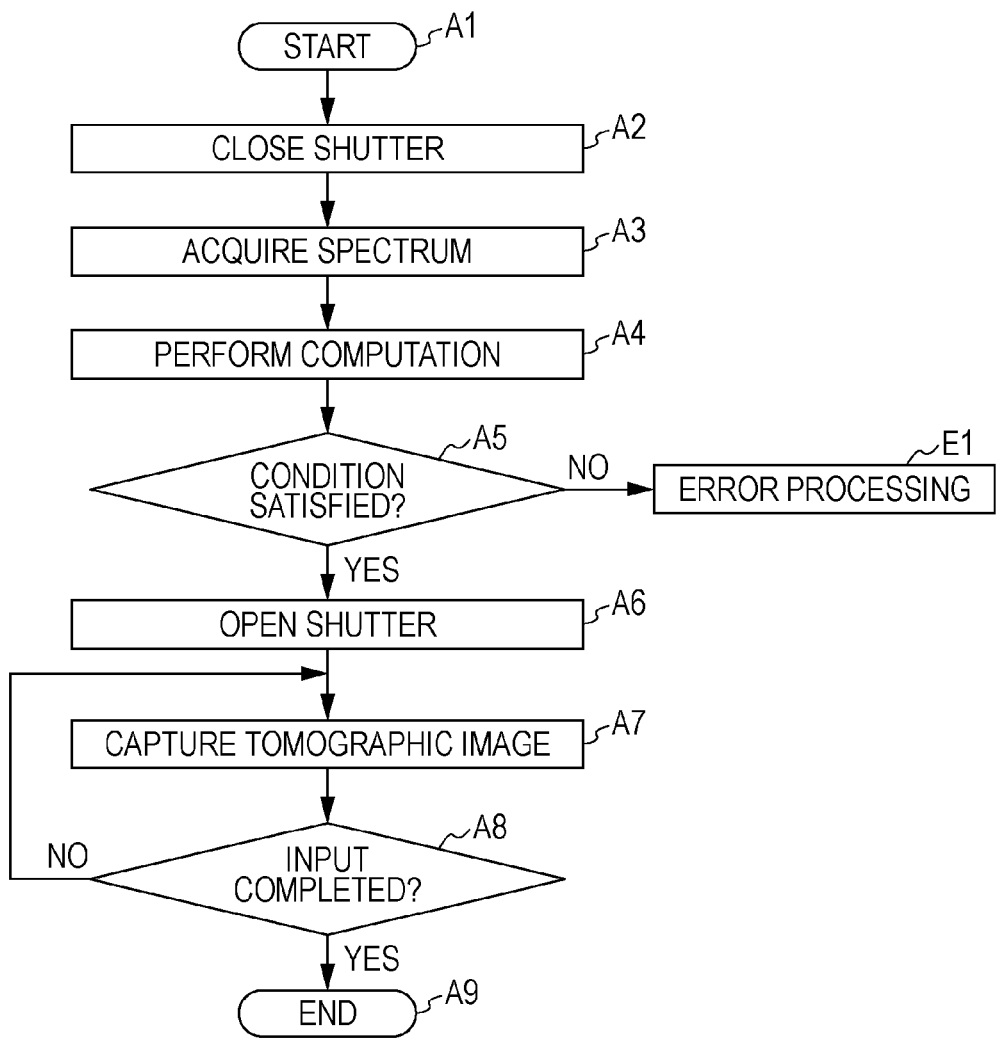
FIG. 2 is a flowchart of the first embodiment of the present invention.

According to the present embodiment, an image pickup method using optical coherence tomography includes at least the following steps a) to e):

a) blocking or changing the optical path of the measurement light beam (e.g., step A1 shown in FIG. 2)

b) generating a light beam (e.g., step A3 shown in FIG. 2)

c) separating the generated light beam into the measurement light beam and the reference light beam (e.g., step A3 shown in FIG. 2)

d) detecting the intensity of the reference light beam (e.g., step A3 shown in FIG. 2)

e) changing a mode in which the optical path of the measurement light beam is blocked or changed to a different mode in accordance with the intensity of the detected reference light beam (e.g., step A6 shown in FIG. 2)

In addition, it is desirable that the image pickup method further include the following steps f) to i):

f) comparing the intensity of the detected reference light beam with a setting value (e.g., step A5 shown in FIG. 2)

g) switching the mode in which the optical path of the measurement light beam is blocked or changed to a different mode (e.g., step A6 shown in FIG. 2)

h) detecting a combined light beam of the returning light from the specimen and the reference light beam (e.g., step A7 shown in FIG. 2)

i) forming a tomographic image from the detected combined light beam (e.g., step A7 shown in FIG. 2)

Note that step a) may be continuously performed by turning on a light source for generating the light beam at all times. In addition, as a method for controlling the image pickup apparatus according to the present embodiment, which defines the sequence of processes performed by the processing unit, steps e) to i) may be performed.

Storage Medium and Program

According to another embodiment, the image pickup method according to the above-described embodiment may be realized in the form of a program to be executed by a computer, and the program may be stored in a computer-readable recording medium (e.g., a flexible disk, a hard disk, an optical disk, a magnetooptical disk, a compact disk-read only memory (CD-ROM), a compact disk recordable (CR-R), a magnetic tape, a nonvolatile memory card, a read only memory (ROM), an electrically erasable programmable read-only memory (EEPROM), or a Blu-ray disk). According to still another embodiment, a program that causes a computer to perform the image pickup method according to the above-described embodiment is provided.

EMBODIMENTS

Embodiments of the present invention are described below.

First Embodiment

Michelson Interferometer

An image pickup apparatus using optical coherence tomography according to a first embodiment is described next with reference to FIG. 1. FIG. 1 is a schematic illustration of an image pickup apparatus using an optical system of a Michelson type (a Michelson interferometer) according to the present embodiment.

A light beam emitted from the light source 101 passes through a lens 103-1 and is separated into the measurement light beam 114 and the reference light beam 113 by the separating unit (a beam splitter) 104. The measurement light beam 114 reaches the eye 119 via the XY scanner 108 and an objective lens 105. Note that the measurement light beam 114 can be blocked by the switching unit (a shutter) 116. The shutter 116 is controlled by the control unit 117. The control unit (a shutter control unit) 117 receives a signal from a computer 112. It is appreciated that hardware different from the computer 112 may transmit the signal to the shutter control unit 117. In such a case, by directly computing data received from the spectrometer 111, the state of the apparatus, such as malfunction, can be detected early.

In the present embodiment, when the measurement light beam 114 is blocked, the return light beam 115 is not generated and, therefore, the measurement light beam 114 does not enter the optical path. As used herein, the term "blocking" refers to not outputting the measurement light beam 114 from the body of the apparatus. In place of disposing a shutter serving as a blocking member in the optical path, the optical path of a light beam may be changed by a mirror, and the light beam may be emitted onto a light shielding member. Alternatively, a member that absorbs a light beam may be disposed. Still alternatively, in some cases, a mirror may be disposed, and the light beam may be returned back along the light path.

When a light path is blocked, the return light beam 115 and a stray light beam can be prevented from entering the light path. As used herein, the term "stray light beam" refers to a light beam emitted from a light emitter, such as a fluorescent lamp, a display, or the sun, regardless of the presence of a specimen.

If blocking of the measurement light beam 114 is deactivated, the measurement light beam 114 passes through the XY scanner 108, the objective lens 105, and a cornea 118 and reaches a retina 120. The measurement light beam 114 is scattered and reflected by the retina 120 so as to form the return light beam 115. The return light beam 115 travels to the beam splitter 104 via the objective lens 105 and the XY scanner 108. In addition, the return light beam 115 is led to the spectrometer 111 via a lens 103-2. The spectrometer 111 includes a lens, a grating, and an image sensor. A charge-coupled device (CCD) line sensor or a complementary metal-oxide semiconductor (CMOS) line sensor is used as the image sensor.

In addition, the reference light beam 113 passes through dispersion compensating glass 107. Thereafter, the reference light beam 113 is reflected by a reference mirror 109 and passes through the dispersion compensating glass 107 again. Thus, the reference light beam 113 returns back to the beam splitter 104. The dispersion compensating glass 107 is used to compensate for the dispersion of the eye and the objective lens 105. The reference mirror 109 can control the optical path length of the reference light beam using a mirror adjusting mechanism 110. Note that in the measurement light beam path, a point at which the reference light beam path length is equal to the measurement light beam path length is referred to as a "coherence gate". When the retina of the eye is examined, the coherence gate is set so as to be close to the retina. The reference light beam 113 and the return light beam 115 are combined by the beam splitter 104, and the combined light beam is led to the spectrometer 111.

A super luminescent diode (SLD), which is a typical low coherent light source, is used as the light source 101. In terms of the wavelength of the light source 101, for example, the center wavelength is 840 nm, and the bandwidth is 50 nm. Note that the bandwidth serves as an important parameter since the bandwidth has an effect on the resolution of the obtained tomographic image in the optical axis direction. In addition, in the present embodiment, an SLD is selected as the light source 101. However, any light source that emits a low coherent light beam can be used. For example, an amplified spontaneous emission (ASE) can be used. In addition, depending on the type of specimen, another light source, such as a halogen lamp, can be used. However, since the wavelength has an effect on the resolution in the transverse direction of the tomographic image, it is desirable that a short wavelength be used if the resolution in the transverse direction is important.

The computer 112 controls the spectrometer 111, the XY scanner 108, the shutter control unit 117, the mirror adjusting mechanism 110, and a focus control mechanism 106. In addition, as general functions of a computer, the computer 112 can receive data, process an image, display an image, and store data.

Image Pickup Method 2

An exemplary image pickup method according to an embodiment of the present invention is described next with reference to a flowchart shown in FIG. 2. In particular, a method for acquiring a spectrum and controlling the shutter is described.

In step A1, measurement is started. In this step, it is desirable the light source 101, the spectrometer 111, the XY scanner 108, the mirror adjusting mechanism 110 be initialized.

Subsequently, in step A2, the shutter 116 is closed. In this mode, a spectrum can be obtained without unwanted stray light appearing in the measurement optical path.

Figure 3:
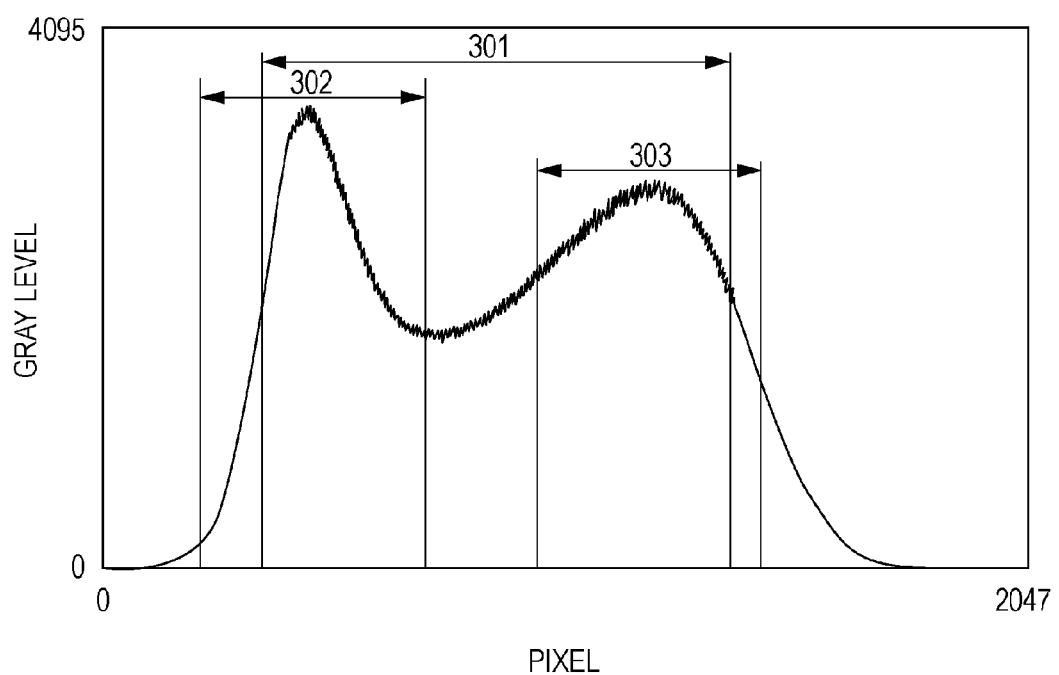
FIG. 3 illustrates spectrum data of the first embodiment of the present invention.

In step A3, a spectrum is acquired. In this step, the shutter 116 is closed, and the reference light beam 113 is acquired. When the line sensor of the spectrometer 111 has 2048 pixels, strength data of 2048 components can be acquired. FIG. 3 illustrates spectrum data of the reference light beam 113, which forms a spectrum shape having two peaks. The abscissa represents a pixel, and the ordinate represents the gray level, which correspond to the wavelength and the intensity of light, respectively. The pixel ranges from 0 to 2047. The gray level is 12 bits and, therefore, it ranges from 0 to 4095. The shape of a spectrum differs in accordance with a light source. In addition, the specification of the line sensor of a spectrometer differs. Accordingly, these values are not limited to the above-described ones. While the present embodiment is described with reference to a spectrometer, a photodiode or an avalanche photodiode can be used when a time domain method or a swept source method is employed.

In step A4, computation is performed on the spectrum obtained in step A3. In the present embodiment, 2048 array data items are averaged. In FIG. 3, the average value is 1437. Note that it is not always necessary that all the items are averaged. For example, the pixels 350 to 1373 may be selected as the first range 301, and the values of the pixels 350 to 1373 may be averaged. At that time, the average value is 2446. By decreasing the range in this manner, the sensitivity of detecting malfunction can be increased.

Furthermore, every predetermined number of pixels may be grouped and averaged. For example, a second range 302 from pixels 200 to 711 and a third range 303 from pixels 980 to 1491 may be set. The average values of the pixels in the two ranges are 2071 and 2436. By separating the pixels into small ranges in this manner, malfunction can be analyzed in more detail. In addition, in stead of averaging, addition or multiplication may be performed. Alternatively, the maximum value, the local maximal value, or the local minimum value may be computed.

In step A5, it is determined whether the resulting value computed in step A4 satisfies a predetermined condition. In the present embodiment, it is determined whether the resulting value computed in step A4 satisfies the setting value (the reference value), that is, whether the resulting value is within the range of the reference value. When the number of the setting values is one and if the resultant value exceeds the setting value, it is determined that malfunction occurs. At that time, the processing proceeds to step E1. For example, it is estimated that the malfunction is caused by excess intensity of light. However, if the resultant value does not exceed the setting value, the processing proceeds to step A6. For example, when the setting value is determined to be 2000 for the average value in the entire range, the value 1437 is lower than the value 2000. Accordingly, the processing proceeds to step A6.

Two setting values can be used. In such a case, setting values 1 and 2 are set so that the setting value 1<the setting value 2. If the resulting value is greater than the setting value 2, it is determined that malfunction occurs, and the processing proceeds to step E1. In such a case, for example, it is estimated that the malfunction occurs in the light source 101. If the resulting value is less than the setting value 1, it is also determined that malfunction occurs, and the processing proceeds to step E1. In such a case, for example, it is estimated that the intensity of light decreases to an insufficient level or the sensitivity of the line sensor of the spectrometer 111 has been degraded. However, if the resultant value is between the setting value 1 and the setting value 2, the processing proceeds to step A6.

A setting value is set for each of the ranges, such as the second range 302 and the third range 303. At that time, if the resulting value does not satisfy one of the setting values, it is determined that malfunction occurs, and the processing proceeds to step E1. In such a case, for example, it is estimated that the line sensor of the spectrometer 111 has been rotated about the optical axis.

In step E1, error processing is performed. In the error processing, it is confirmed that the shutter 116 is closed, and an error message is displayed. Thereafter, the light source is turned off as needed, and a completion process is performed.

In step A6, the shutter 116 is made open. In this step, a measurement light beam is emitted to the specimen. The return light beam enters the measurement optical path, and the combined light beam can be measured.

In step A7, a tomographic image is captured. In this step, alignment processes, such as alignment of the coherence gate, focus control, and visual fixation, are performed. Subsequently, a tomographic image is captured. The spectrum is obtained in synchronization with the movement of the XY scanner 108. If the image is captured with the XY scanner 108 being continuously moved along one axis (e.g., the X-axis), a two-dimensional image can be obtained. When the X direction is set to Fast-Axis and the Y direction is set to Slow-Axis and if the image is captured, a three-dimensional image can be captured. After the process in step A7 is completed, the processing proceeds to step A8.

Generally speaking, a tomographic image can be obtained as follows. First, data items acquired from a line sensor that are evenly spaced with respect to the wavelength are converted into a wavenumber spectrum in which data items are evenly spaced with respect to the wavenumber. Subsequently, a fast Fourier transform (FFT) process is performed, and a required range is retrieved. At that time, noise is removed, and image correction is performed as needed. In addition, all image processing may be performed after the data items are acquired.

In step A8, it is determined whether input of data into the computer 112 by an examiner is completed or not. If the image of the other eye is captured or if the image of the eye of another person is captured, the processing returns to A7, where another tomographic image is captured. If the process is to be completed, the processing proceeds to step A9.

In step A9, the measurement is completed. At that time, it is desirable that the light source 101, the spectrometer 111, the XY scanner 108, the mirror adjusting mechanism 110, and the focus control mechanism 106 are initialized.

In this way, by using the data acquired from the line sensor of the spectrometer 111 that captures a tomographic image, the state of the measurement light beam and the occurrence of malfunction of the apparatus can be determined, and the shutter 116 can be open or closed. Accordingly, additional hardware is not required and, therefore, the cost of the apparatus is not increased. In particular, since the state of the measurement light beam and the occurrence of malfunction of the apparatus can be detected by using only the measurement values obtained from the line sensor, the state of the measurement light beam and the occurrence of malfunction of the apparatus can be more correctly detected.

Second Embodiment

Detection of Malfunction at Startup Time and Prior to Measurement

Figure 4:
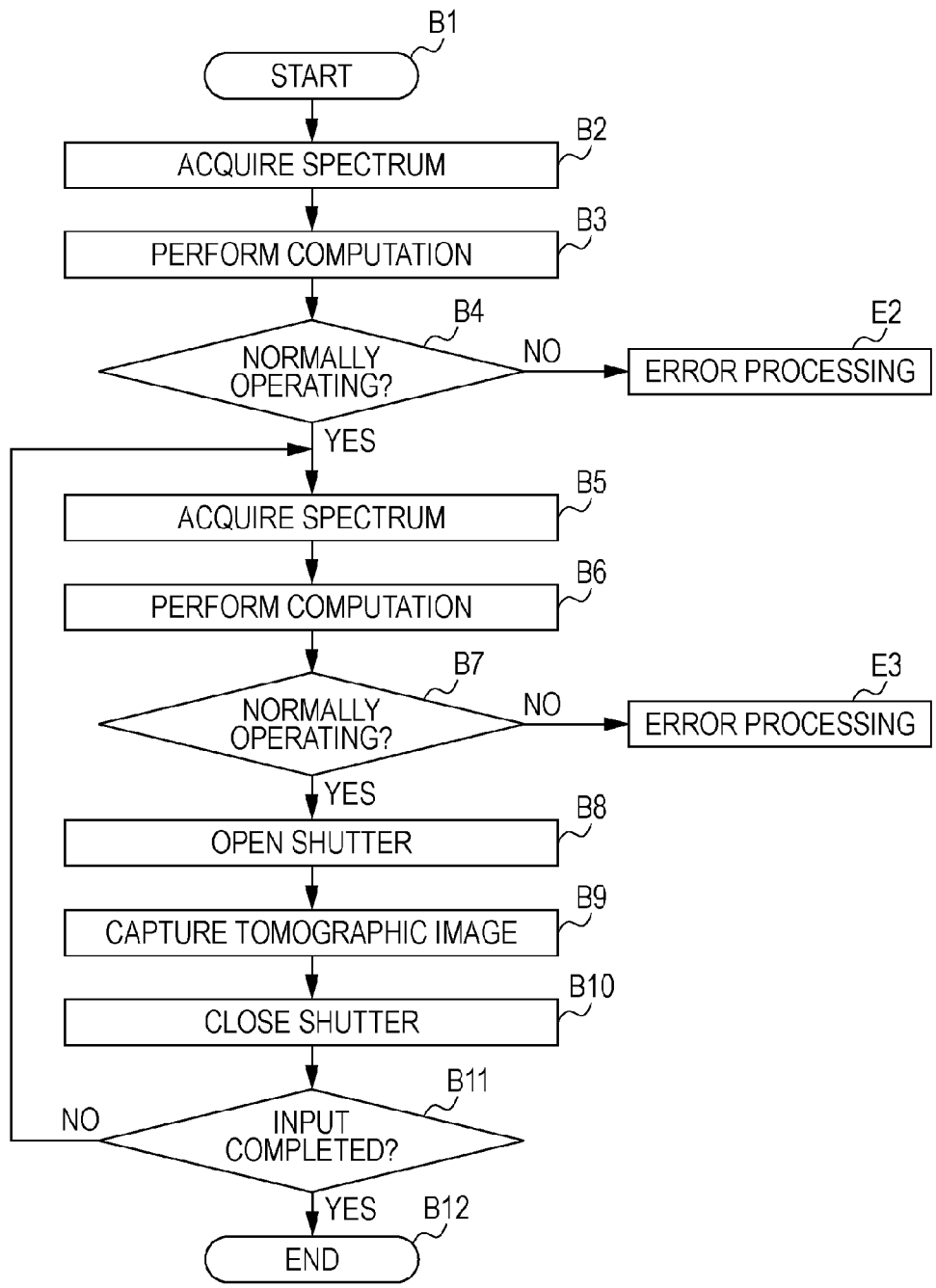
FIG. 4 is a flowchart of a second embodiment of the present invention.

An image pickup method using optical coherence tomography according to a second embodiment is described next with reference to FIG. 4. In particular, acquisition of a spectrum and control of a shutter are described. In the present embodiment, a difference between the first embodiment and the present embodiment is mainly described. The present embodiment differs from the first embodiment in that the state of the apparatus is detected at a startup time and prior to measurement.

When the apparatus is started, the apparatus is not frequently in the steady state, since the line sensor of the spectrometer 111 and the light source are not sufficiently warmed up. Accordingly, the reliability of detecting the state may be decreased. In addition, if the state is detected only at a startup time, the occurrence of malfunction during use cannot be detected. However, if the state is detected in detail at every detection time, much time is required. Accordingly, it is efficient if the state is detected in detail at a startup time and, subsequently, only simple malfunction detection is performed.

In step B1, measurement is started.

In step B2, the spectroscopic spectrum is acquired. When the spectrum is acquired, it is desirable that the measurement be performed after a warming up operation (an operation performed for a certain period of time under low load conditions) is performed for about 10 minutes and the apparatus enters a normal state. In this step, the measurement light beam 114 is blocked, and no return light beam 115 output from a specimen is measured.

In step B3, computation is performed on the spectrum obtained in step B2. First, the acquired spectrum is separated for each of a predetermined number of pixels. At that time, the spectrum is separated into 8 sections, each including 256 pixels. The average value is computed for each of the ranges. Thereafter, the local maximum value and the local minimum value are obtained. In addition, the derivative value of the spectrum is computed. In the present embodiment, a difference in value between a pixel and the neighboring pixel is computed.

In step B4, it is determined whether the apparatus malfunctions. For example, if the average value for each of the sections is within a predetermined range, it is determined that the apparatus does not malfunction at a startup time. In addition, if each of the pixel positions of the local maximum value and the local minimum value, the gray level, and the derivative value is within a predetermined setting range, it is determined that the apparatus does not malfunction at a startup time, and the processing proceeds to step B5. However, if these conditions are not satisfied, the processing proceeds to step E2, where error processing is performed.

In step E2, it is determined whether the shutter 116 is closed. If necessary, the completion process of the apparatus is performed. First, the gray level of each of the sections is compared with the setting value of the section. If some or all of the gray levels are lower than the setting values, it is estimated that the light source 101 has been degraded or the sensitivity of the line sensor of the spectrometer 111 has been degraded. However, if some or all of the gray levels are higher than or equal to the setting values, it is estimated that the transmission ratio is increased due to, for example, loss of one of the optical components. As the number of the sections increases, the accuracy of detection of the state can be increased.

Subsequently, by comparing each of the pixel positions of the local maximum value and the local minimum value with the predetermined value thereof, it can be estimated that the position of the line sensor has been shifted or the focus of the spectrometer 111 has been shifted. Since a pixel of the line sensor of the spectrometer 111 is as small as 10 micrometers in size, the position of the pixel is easily shifted by a change in temperature. Thus, such failure may occur.

In addition, using the derivative value of the spectrum, it can be estimated that a circuit of the line sensor of the spectrometer 111 malfunctions. If noise increases due to degradation of a circuit component or an inappropriate layout of a ground line, such failure may occur.

In step B5, a spectrum is acquired. From this step, the state of the apparatus is detected prior to acquisition of a tomographic image, not at the startup time.

In step B6, computation is performed on the spectrum obtained in step B5. In this case, simple computation is sufficient, since accurate measurement has been performed at the startup time. Each of the local maximum value and the local minimum value is compared with the setting value thereof. Note that in general, patient information is input before a tomographic image is captured. Accordingly, the state of the apparatus can be detected at that time.

In step B7, it is determined whether the apparatus malfunction. In this step, if one of the average value of pixel strength signals, the local maximum value, and the local minimum value, and the derivative value in each section is within a setting range, the processing proceeds to step B8. If the value is outside the setting range, the processing immediately proceeds to step E3.

In step B8, the shutter 116 is made open.

In step B9, a tomographic image is captured. In this step, alignment processes, such as alignment of the coherence gate, focus control, and visual fixation, are performed. Subsequently, a tomographic image is captured. The spectrum is obtained in synchronization with the movement of the XY scanner 108.

In step B10, the shutter 116 is closed. This is done because when the processing returns to step B5 after the subsequent step B11 is performed, a spectrum is acquired with the shutter 116 closed.

In step B11, it is determined whether input of data into the computer 112 by an examiner is completed or not. If the image of the other eye is captured or if the image of the eye of another person is captured, the processing returns to B5, where another tomographic image is captured. If the process is to be completed, the processing proceeds to step B12.

In step B12, the measurement is completed.

According to the present embodiment, the state of the apparatus is accurately detected at a startup time, and the state of the apparatus is simply detected prior to measurement. Accordingly, a correct and reproducible tomographic image can be captured regardless of when the tomographic image is captured. In addition, if the apparatus malfunctions, the measurement light beam can be prevented from traveling to the outside of the apparatus by controlling the shutter 116.

Third Embodiment

Mach-Zehnder Interferometer

Figure 5:
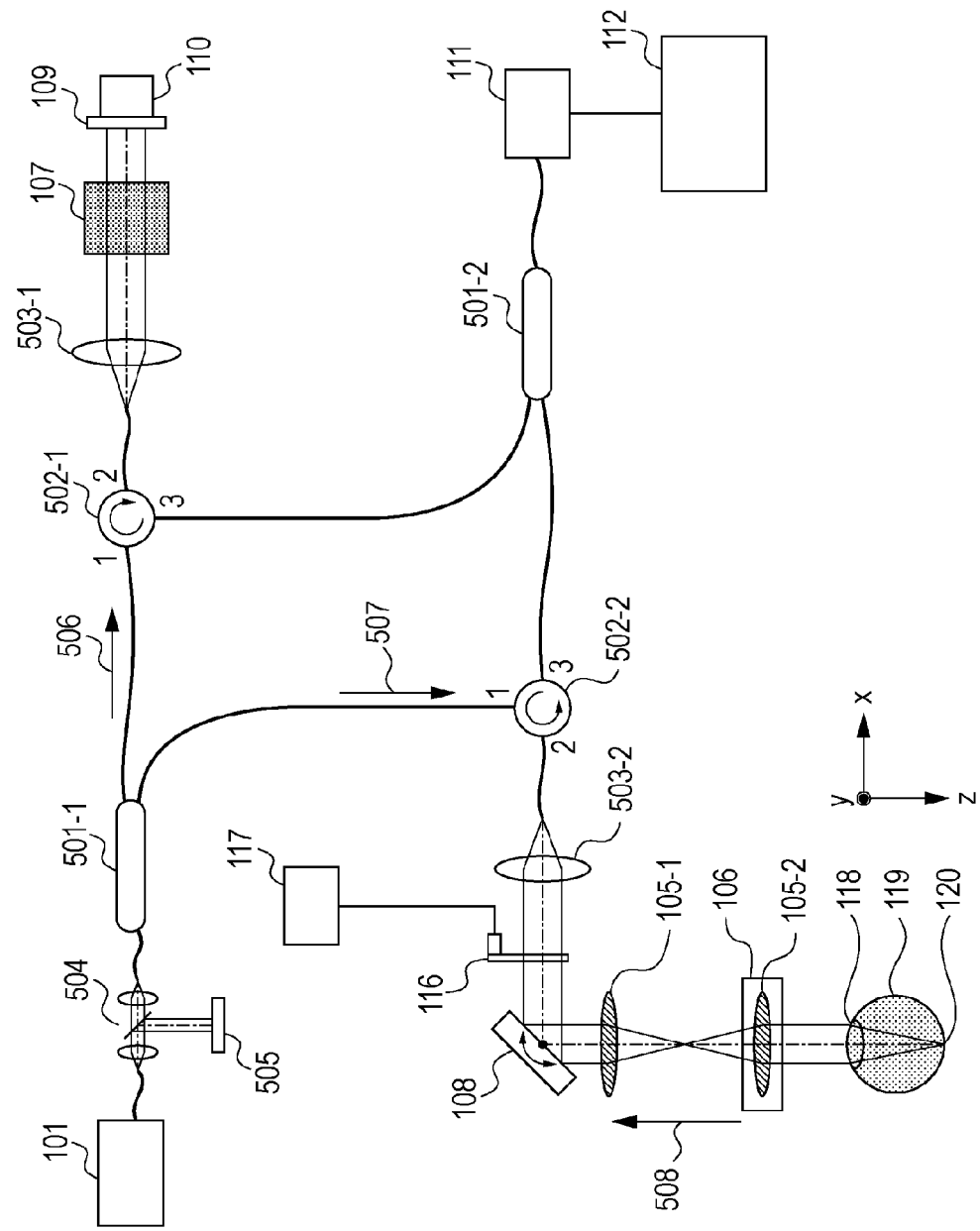
FIG. 5 is a diagram illustrating an optical system of an image pickup apparatus according to a third embodiment of the present invention.

An image pickup apparatus using optical coherence tomography according to a third embodiment is described next with reference to FIG. 5. FIG. 5 is a schematic illustration of the image pickup apparatus using an optical system of a Mach-Zehnder type (a Mach-Zehnder interferometer) according to the present embodiment. A difference between the present embodiment and the first embodiment is mainly described. This optical system further includes a unit for determining whether the light source malfunctions.

A light beam emitted from the light source 101 passes through an optical splitter 504 and a fiber coupler 501-1 and is separated into a measurement light beam 507 and a reference light beam 506. The light beam separated by the optical splitter 504 is detected by a detector 505. In the present embodiment, the power of the light source is detected using a photodetector. A detection signal is input to the computer 112. When the light source includes a power monitor, the output of the power monitor may be input to the computer 112. Note that a different hardware may be used in place of the computer 112.

The measurement light beam 507 is input to a first port of a circulator 502-2 and is output from a second port of the circulator 502-2. Thereafter, the measurement light beam 507 reaches a lens 503-2. When blocking of light performed by the shutter 116 is deactivated, the measurement light beam 507 passes through the XY scanner 108, the objective lens 105, and the cornea 118 and reaches the retina 120. The measurement light beam 507 is scattered and reflected and forms a return light beam 508. The return light beam 508 passes through the objective lens 105 and the XY scanner 108 in the opposite direction and enters the second port of the circulator 502-2. Thereafter, the return light beam 508 is output from a third port of the circulator 502-2 and reaches a fiber coupler 501-2.

In addition, the reference light beam 506 passes through a circulator 502-1, a lens 503-1, and the dispersion compensating glass 107 and is reflected by the reference mirror 109. The reflected reference light beam 506 returns back to the lens 503-1 and the circulator 502-1 through the dispersion compensating glass 107. Thereafter, the reference light beam 506 reaches the fiber coupler 501-2. The reference mirror 109 can adjust the optical path length using the mirror adjusting mechanism 110. The reference light beam 506 and the return light beam 508 are combined by the fiber coupler 501-2, and the combined light beam is led to the spectrometer 111.

The case in which the measurement light beam 507 is blocked by the shutter 116 is described next. The shutter 116 is controlled by the shutter control unit 117. A signal for controlling the shutter 116 is output from the computer 112 to the shutter control unit 117. When the optical path is blocked by the shutter 116, the return light beam 508 is not generated and, therefore, the return light beam 508 does not enter the optical path. Accordingly, by measuring the spectrum using the spectrometer 111 with the return light beam 508 blocked, the spectrum of the reference light beam 506 can be detected. If the spectrum indicates a normal state, one of the average value of pixel strength signals, the local maximum value, and the local minimum value, and the derivative value in each section is within the setting range as described in the first and second embodiments. However, if the computed value is outside the setting range, an error message is displayed. At that time, it is determined whether the output of the detector 505 is within a predetermined range. If the output of the detector 505 is within a predetermined range, it can be determined that the light source 101 does not malfunction. However, if the output of the detector 505 is outside the predetermined range, it can be determined that the light source 101 malfunctions.

Note that in place of the shutter 116, the XY scanner 108 can be used to provide a shutter function. However, the specification of the XY scanner 108 may be changed. The XY scanner 108 can change a direction in which a light beam travels using the offset thereof. If the light direction is controlled so that the light direction is outside a field stop (not shown), the light beam is not output from the housing. In this case, external stray light does not reach the spectrometer 111.

In addition, if a mirror is used as the shutter 116, the measurement light beam 507 is reflected. Accordingly, the spectrometer 111 detects a combined light beam of the measurement light beam 507 and the reference light beam 506. In such a case, if the position of the reference mirror is changed, the coherence state is changed. In a normal state, if the reference mirror 109 stays at the same position, the detected combined light beam is reproducible. That is, when control is performed so that the reference mirror 109 stays at the same position and if one of the average value of pixel strength signals, the local maximum value, and the local minimum value, and the derivative value in each section is not within the setting range, it can be determined that malfunction due to a state change of the optical path has occurred.

According to the present embodiment, in order to identify the cause of malfunction, a unit for verifying a signal of the light source 101 is additionally provided. Thus, malfunction of the light source can be distinguished from malfunction of another component. If malfunction occurs, the measurement light beam can be prevented from being output to the outside by controlling the shutter 116.

Fourth Embodiment

Multi-Beam Based Optical System

Figure 6A:
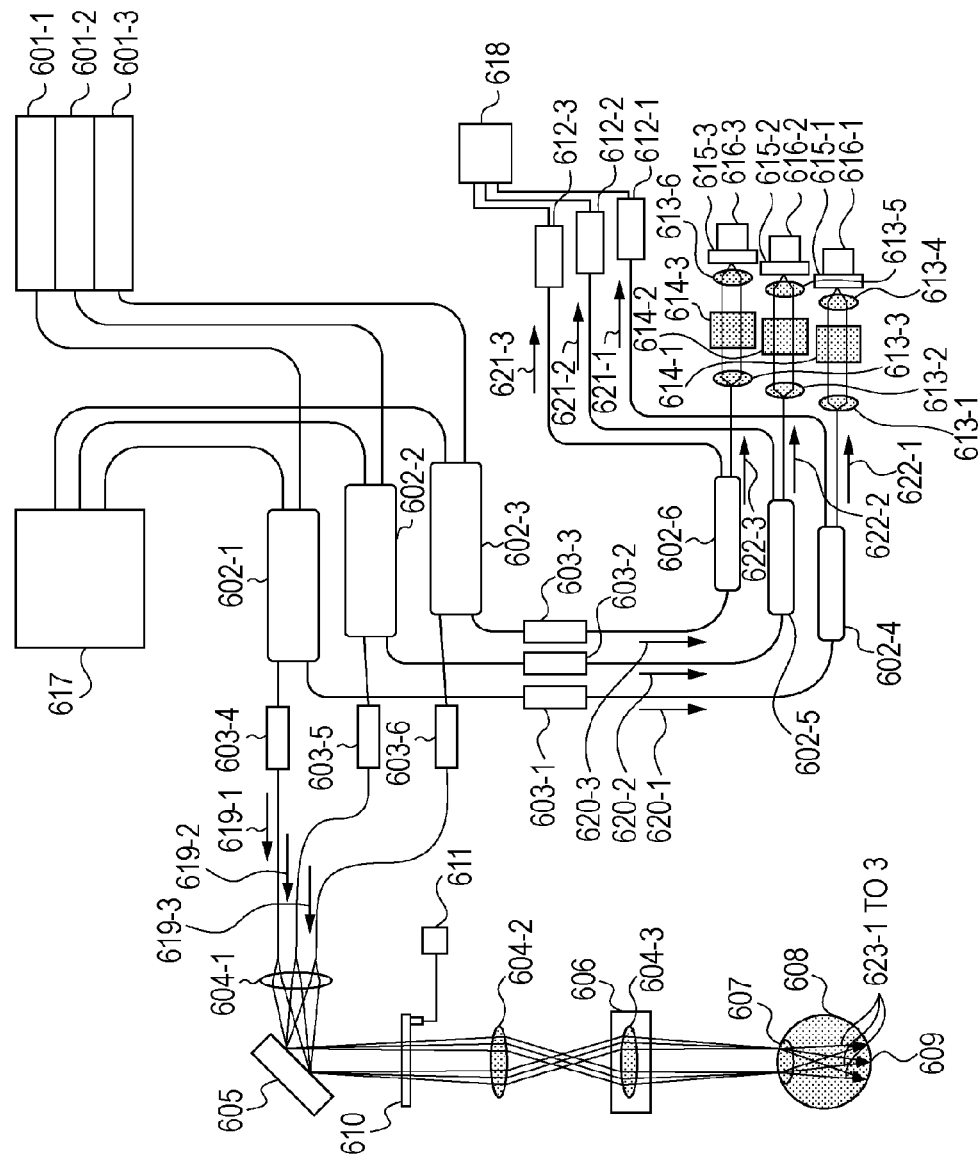
FIG. 6A is a diagram illustrating an optical system of an image pickup apparatus according to a fourth embodiment of the present invention.

An image pickup apparatus using optical coherence tomography (an OCT apparatus) according to a fourth embodiment is described next with reference to FIG. 6A. As shown in FIG. 6A, the whole OCT apparatus according to the present embodiment functions as a Michelson interferometer.

That is, each of light beams emitted from a plurality of light sources is separated into a measurement light beam and a reference light beam. Thereafter, the measurement light beam passes through its own measurement optical path and is emitted onto a specimen. The return light beam of each of the measurement light beams is combined with the reference light beam. Thus, optical coherence occurs. By using such a plurality of combined light beams, an OCT system captures a tomographic image of a specimen. The OCT apparatus includes such an OCT system.

More specifically, light beams emitted from a plurality of light sources 601-1 to 601-3 are separated into measurement light beams 619-1 to 619-3 and reference light beams 620-1 to 620-3 by fiber couplers 602-1 to 602-3, respectively. In addition, the reference light beams 620-1 to 620-3 pass through polarization adjustment devices 603-1 to 603-3 and are separated into light beams for detecting the intensity of light (light intensity detection light beams) 621-1 to 621-3 and reference light beams 622-1 to 622-3 by the fiber couplers 602-4 to 602-6 (also referred to as "reference beam separating units"), respectively. The light intensity detection light beams 621-1 to 621-3 are detected by detectors 612-1 to 612-3 (also referred to as "light intensity detection light beam detecting units"), respectively. In the present embodiment, photodetectors are used as the detectors 612-1 to 612-3. Signals indicating the intensities of the light beams output from the detectors 612-1 to 612-3 are input to a computer 618. Note that in place of the computer 618, a dedicated hardware may be used.

The measurement light beams 619-1 to 619-3 pass through the polarization adjustment devices 603-4 to 603-6, respectively. Thereafter, the measurement light beams 619-1 to 619-3 are made incident on an XY scanner 605 via an objective lens 604-1. For simplicity, the description has been made with reference to the XY scanner 605 being a single mirror. However, in reality, an X scanning mirror and a Y scanning mirror may be disposed so as to be close to each other and may perform a raster scan over a retina 609 in a direction that is perpendicular to the optical axis. In addition, the positions of the objective lenses 604-1 and 604-2 are adjusted so that each of the centers of the measurement light beams 619-1 to 619-3 is aligned with the rotation center of the mirror of the XY scanner 605.

A light beam output from the XY scanner 605 reaches the retina 609 via the objective lens 604-2, an objective lens 604-3, and a retina 607 of an eye 608 to be examined. Return light beams 623-1 to 623-3 scattered and reflected by the retina 609 return to the fiber couplers 602-1 to 602-3 via the objective lenses 604-2 and 604-3, the XY scanner 605, and the objective lens 604-1. Note that the measurement light beams 619-1 to 619-3 can be blocked by a shutter 610. In addition, the objective lens 604-3 can be moved in the optical axis direction by a focus control unit 606.

In addition, the reference light beams 620-1 to 620-3 pass through lenses 613-1 to 613-3 and dispersion compensating glass members 614-1 to 614-3 and are collected onto reference mirrors 615-1 to 615-3 by lenses 613-4 to 613-6.

Subsequently, the traveling directions of the reference light beams 622-1 to 622-3 are changed by the reference mirrors 615-1 to 615-3. Thereafter, the reference light beams 622-1 to 622-3 return back to fiber couplers 602-4 to 602-6 via the lenses 613-4 to 613-6, the dispersion compensating glass members 614-1 to 614-3, and the lenses 613-1 to 613-3, respectively. The reference light beams 622-1 to 622-3 then pass through the polarization adjustment devices 603-1 to 603-3 and reach the fiber couplers 602-1 to 602-3. The dispersion compensating glass members 614-1 to 614-3 are used for compensating for the dispersion occurring when the measurement light beams 619-1 to 619-3 travel back and forth through the eye 608 to be examined with respect to the reference light beams 622-1 to 622-3. Furthermore, the optical path lengths of the reference light beams 622-1 to 622-3 can be controlled by mirror adjustment mechanisms 616-1 to 616-3, respectively. The reference light beams 622-1 to 622-3 are combined with the return light beams 623-1 to 623-3 by the fiber couplers 602-1 to 602-3, respectively, and are led to a spectrometer 617.

When the measurement light beams 619-1 to 619-3 are blocked by the shutter 610, the shutter 610 is controlled by a shutter control mechanism 611. A control signal for controlling the shutter 610 is output from the computer 618. In a normal mode, the outputs of the detectors 612-1 to 612-3 are within the ranges set in the first to third embodiments, respectively. If the outputs of the detectors 612-1 to 612-3 are outside the ranges, an error message is displayed, and the measurement light beams 619-1 to 619-3 are blocked by the shutter 610.

By separating the reference light beam, detecting the intensities of light beams separated from the reference light beam, and determining whether the intensities are normal, it can be determined whether the apparatus is in a normal state without affecting the measurement light beam, that is, without decreasing the quality of the image.

By employing the above-described configuration and detecting part of the reference light beam in the reference light path, a light beam that has lost an amount of light smaller than an amount of light lost when the measurement light beam is made incident on the specimen can be used to detect the intensity of light. Accordingly, the light beam emitted from the light source can be efficiently used.

In addition, by separating a light intensity detection light beam from the reference light beam when the reference light beam travels towards the reference mirror, the intensity of the reference light beam that varies little can be detected. That is, it can be correctly determined whether the apparatus operates normally. Note that the reference light beam reflected by the reference mirror may be separated to generate a light beam used for detecting the intensity of light.

Fifth Embodiment

Wavelength Selection Reflecting Unit

Figure 6B:
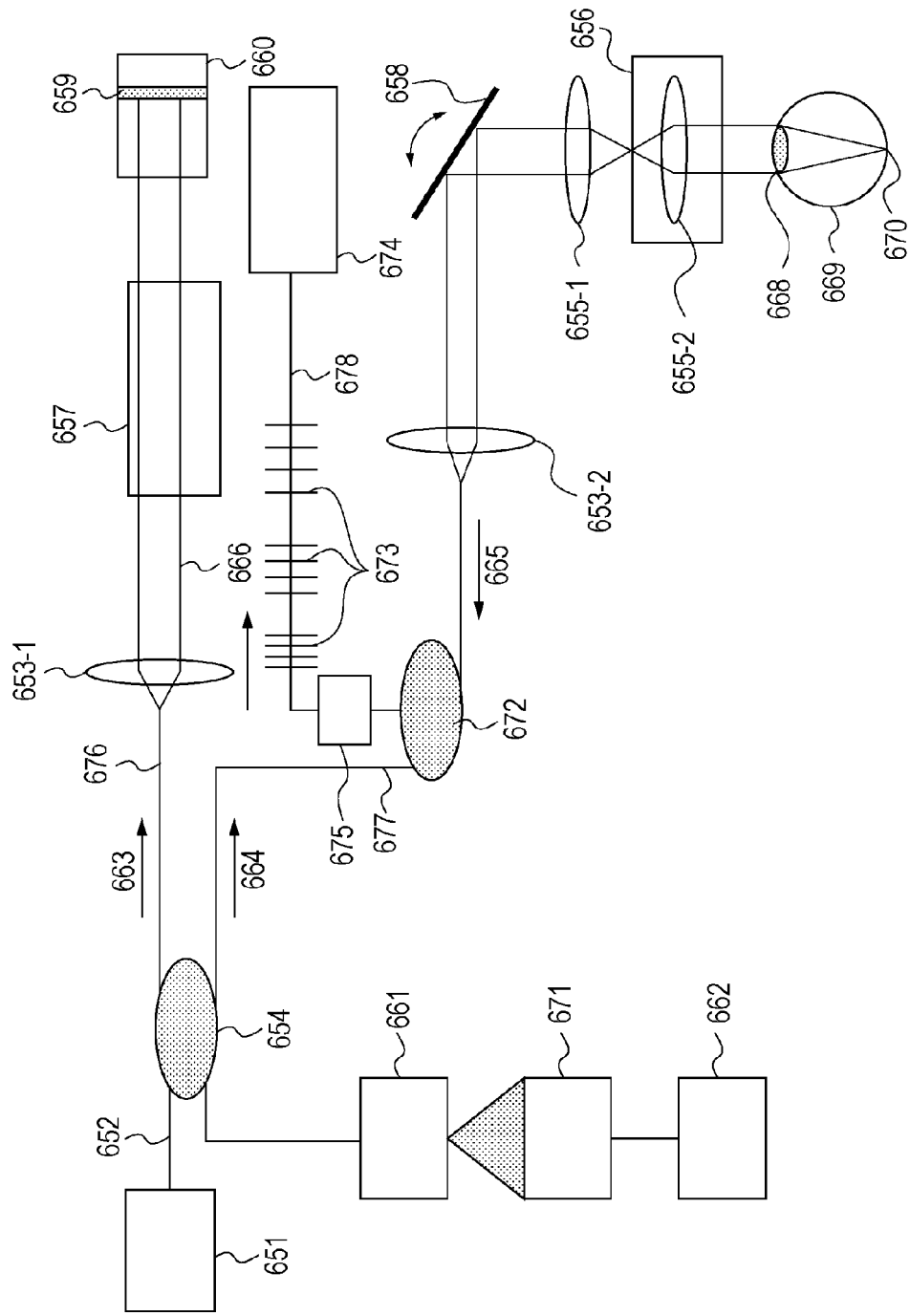
FIG. 6B is a diagram illustrating an optical system of an image pickup apparatus according to a fifth embodiment of the present invention.

An image pickup apparatus using optical coherence tomography according to a fifth embodiment is described next with reference to FIG. 6B. FIG. 6B illustrates an image pickup apparatus that uses a Michelson interferometer. A light beam emitted from a light source 651 passes through a fiber 652. Thereafter, the light beam is separated into a reference light beam 663 that travels through a reference arm 676 and a measurement light beam 664 that travels through a sample arm 677 by a beam splitter 654, such as a fiber coupler. The measurement light beam 664 and the reference light beam 663 travel in the fiber 652 until they are transmitted to the air by a lens 653.

The reference light beam 663 passes through dispersion compensating glass 657. Thereafter, the reference light beam 663 is reflected by a reference mirror 659. Subsequently, the reference light beam 663 passes the dispersion compensating glass 657 again and returns to the beam splitter 654. The reference mirror 659 is movable so that a mirror control mechanism 660 can control the optical path length of the reference light path.

The measurement light beam 664 is separated by a beam splitter 672 (also referred to as a "measurement light beam separating unit"). Like the above-described embodiment, one of the separated light beams passes through an XY scanner 658, objective lenses 655-1 and 655-2 and reaches an eye 669 (a specimen). Note that the objective lens 655-2 is movable in the optical axis direction by a focus control mechanism 656.

The other light beam separated by the beam splitter 672 serves as an inspection light beam 666. An inspection light beam propagating unit 678 is used for detecting the state of the OCT apparatus. The inspection light beam propagating unit 678 includes a plurality of fiber Bragg gratings 673 (also referred to as a "wavelength selection reflecting unit"), a preventing unit 674 that prevents the inspection light beam 666 that has passed through the fiber Bragg gratings 673 from being reflected towards the beam splitter 672 (also referred to as a "measurement light beam separating unit"), and a control member 675 that controls return inspection light beams output from the plurality of fiber Bragg gratings 673. Any member that prevents reflection can be used as the preventing unit 674. More specifically, an antireflection film or a light absorbing element can be used. Alternatively, a mechanism that changes the traveling direction of a light beam to a different direction, such as a circulator or a light switch, can be used.

The fiber Bragg gratings 673 are described below. A fiber Bragg grating is a fiber having a function of accurately and precisely reflecting a light beam having a particular wavelength. By emitting an ultraviolet ray into a fiber through a phase mask and introducing periodical refractive-index modulation into the core of a fiber, a fiber Bragg grating is generated. The wavelength of a light beam reflected by a fiber Bragg grating varies in accordance with a period of refractive-index modulation of the core of the fiber Bragg grating. In a fiber Bragg grating, the period of refractive-index modulation varies in accordance with thermal expansion due to an increase in the temperature of the fiber and a variation in stress due to pulling of the fiber. With a variation in the period of refractive-index modulation, the wavelength interval of a reflected light beam varies. Typically, a fiber Bragg grating has a temperature dependency having a reflection peak characteristic of 0.01 nm/degrees (Celsius). More specifically, thermal extension caused by a temperature increase of 10 degrees (Celsius) shifts the reflection peak to the long wavelength side by 0.1 nm. According to the present embodiment, this phenomenon is used. Therefore, a change in states of the light source and the spectrometer can be detected in addition to a change in state of a sample arm of the OCT apparatus.

Figure 7A:
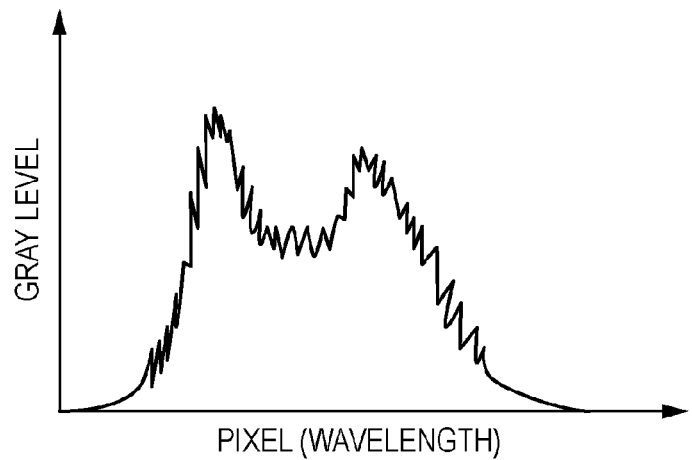
FIG. 7A illustrates spectrum data of the fifth embodiment of the present invention.
Figure 7B:
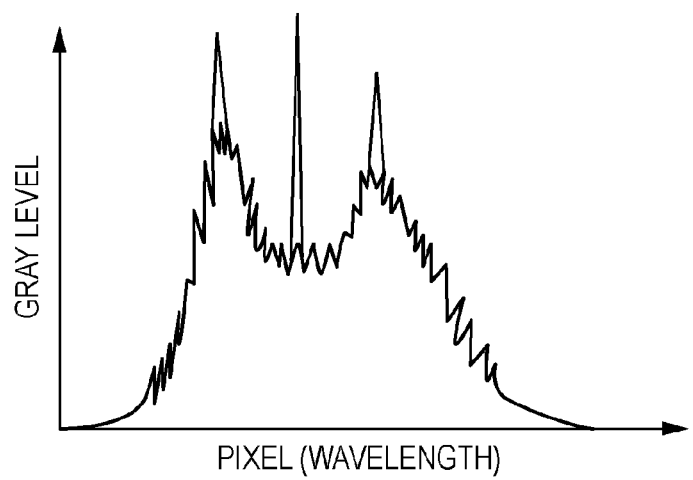
FIG. 7B illustrates spectrum data of the fifth embodiment of the present invention.

The above-described phenomenon is described in more detail next with reference to FIGS. 6B, 7A, and 7B. FIG. 7A illustrates an example of an interference signal of the OCT apparatus. The abscissa represents a sensor pixel, which corresponds to wavelengths spectrally separated by a spectrometer 661. The ordinate represents the intensity (the gray level) of the light beam. At that time, when the inspection light beam reflected by the fiber Bragg gratings 673 is overlaid on the interference signal, an interference signal as shown in FIG. 7B appears. That is, an interference signal having peaks 701, 702, and 703 appears. In addition, it is desirable that a distance between the fiber coupler 654 and the reference mirror be substantially the same as a distance between the fiber coupler 654 and any one of the fiber Bragg gratings 673. Note that the light beams spectrally separated by the spectrometer 661 are detected by a sensor 671 in the form of the intensities of the individual wavelengths. In addition, the detected intensities are stored in a computer 662.

At that time, it is desirable that the branch ratio of the beam splitter 672 be adjusted so that the intensity of light branched to the retina increases. This is because the reflection intensity of the fiber Bragg grating 673 is much higher than that of a retina 670. For example, it is desirable that the branch ratio of the beam splitter 672 be set to 99:1 ("99" for the branched light beam made incident on the retina). Therefore, according to the present embodiment, loss of a measurement light beam in the inspection light beam propagating unit 678 has little effect.

Figure 7C:
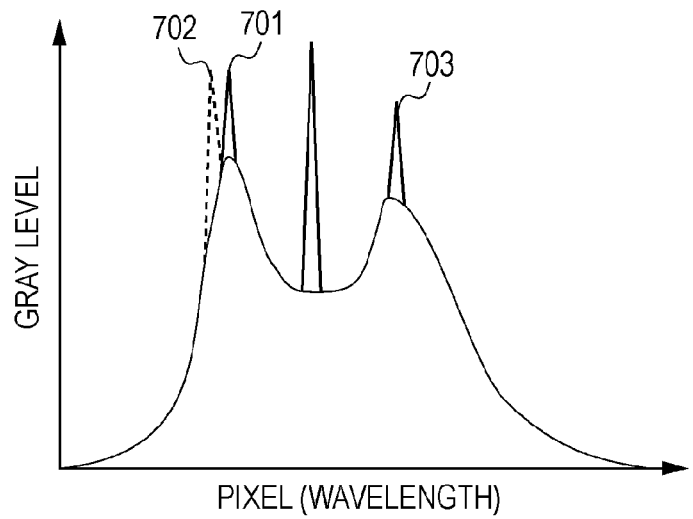
FIG. 7C illustrates spectrum data of the fifth embodiment of the present invention.

An increase in the temperature inside the fiber caused by the sample arm is discussed below. At that time, the period of refractive-index modulation of the fiber Bragg grating 673 physically connected to the sample arm is changed and, therefore, the reflection peak wavelength is shifted. Thus, as shown in FIG. 7C, an overlaid return inspection light beam is made incident on a sensor pixel that is different from that in a normal case. As a result, the peak of the interference signal varies. By providing the plurality of fiber Bragg gratings 673, the state of the OCT apparatus can be detected in more detail.

More specifically, as shown in FIG. 7C, if only one of the return inspection light beams is shifted from a pixel on which the return inspection light beam is made incident in a normal case (the peak 701 is shifted to the peak 702 on the left), the spectrometer or part of the sensor may malfunction. In addition, if the return inspection light beams are shifted from pixels on which the return inspection light beams are made incident in a normal case in the same direction (e,g., if three peaks shown in FIG. 7C are shifted to the long wavelength side), an abnormal temperature of the fiber or shift of the entire sensor may occur. Furthermore, if the return inspection light beams are shifted from pixels on which the return inspection light beams are made incident in a normal case in opposite directions (e,g., if the peak 703 shown in FIG. 7C is shifted to the long wavelength side and the peak 701 is shifted to the short wavelength side), the spectrometer may malfunction. Still furthermore, if the intensity of the return inspection light beam is modulated, the light source may malfunction or the sensitivity of the sensor may be degraded. In this way, the cause can be roughly determined by the amount of variation in the peak intensity of the return inspection light beam in the interference signal.

As described above, by examining the return inspection light beams reflected by the fiber Bragg gratings, the cause of malfunction of the OCT apparatus can be examined in detail. In addition, for that reason, it is desirable that a plurality of fiber Bragg gratings be provided.

The control member 675 that controls the return inspection light beams is described next. In order to accurately and precisely detect malfunction of the sample arm and the light source, it is desirable that an inspection light beam propagating unit 678 be physically connected to the sample arm. In addition, when the eye 669, which is a specimen, is measured, it is desirable that the return inspection beam be not overlaid by an interference signal, as shown in FIG. 7A. In addition, in order to increase the intensity of the returning inspection beam, the control member 675 is necessary.

More specifically, a difference between the levels of each of the pixels shown in FIGS. 7B and 7A can be obtained. If an interference signal contains a time-varying component, a signal shown in FIG. 7A is acquired a plurality of number of times and the acquired signals are averaged. In this way, the variation of component with time can be suppressed to some extent. Alternatively, by disposing a polarized wave controller in the control member 675, interfere of the reference light beam with the measurement light beam can be prevented. By intentionally shifting the polarized wave plane from the reference light beam and the measurement light beam using the polarized wave controller 675, overlay of the return inspection light beam on the interference signal can be prevented. Alternatively, by using an optical fiber switch, a direction in which the return inspection light beam travels can be changed when a specimen is measured.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-151484, filed Jun. 25, 2009 and No. 2010-061054, filed Mar. 17, 2010, which are hereby incorporated by reference herein in their entirety.

The invention claimed is:

1. An image pickup apparatus for capturing an image of an object comprising:
    a scanner configured to scan the object with a measurement beam;
    an optical system configured to irradiate the object the measurement beam via the scanner and to form a combined beam by combining a reference beam and a return beam returned from the object irradiated with the measurement beam;
    a detector configured to detect an intensity of the reference beam or an intensity of the combined beam;
    a controller configured to control the scanner such that an optical path of the measurement beam is changed to lead the measurement beam to the object in a case where the detected intensity of the reference beam is less than a threshold or not to lead the measurement beam to the object in a case where the detected intensity of the combined beam is higher than a threshold.

2. The image pickup apparatus according to claim 1, further comprising:
    a wavelength selection reflecting unit configured to receive an inspection beam obtained by separating the measurement beam;
    wherein the detector detects a combined beam of a return inspection beam reflected from the wavelength selection reflecting unit and the reference beam.

3. The image pickup apparatus according to claim 2, further comprising a measurement beam separating unit configured to separate the measurement beam and obtain the inspection beam,
    wherein an optical path starting from the measurement beam separating unit to the wavelength selection reflecting unit is formed from a fiber, and wherein the wavelength selection reflecting unit is formed from a plurality of fiber Bragg gratings.

4. The image pickup apparatus according to claim 1, wherein the object is an eye, and
    wherein, while the scanner scans the eye with the measurement beam, a retina of the eye is irradiated with the measurement beam via a cornea of the eye so that an image of the retina is captured.

5. An image pickup method for capturing an image of an object, comprising:
    scanning, using a scanner, the object with a measurement beam;
    irradiating the object with the measurement beam via the scanner and forming a combined beam by combining a reference beam and a return beam returned from the object irradiated with the measurement beam;
    detecting an intensity of the reference beam with a detector or an intensity of the combined beam with the detector; and
    controlling the scanner such that an optical path of the measurement beam is changed to lead the measurement beam to the object in a case where the detected intensity of the reference beam is less than a threshold or not to lead the measurement beam to the object in a case where the detected intensity of the combined beam is higher than a threshold.

6. A non-transitory computer-readable medium storing thereon a computer-executable program, that when executed by a processor, performs the steps comprising:
scanning, using a scanner, the object with a measurement beam;
irradiating the object with the measurement beam via the scanner and forming a combined beam by combining a reference beam and a return beam returned from the object irradiated with the measurement beam;
detecting an intensity of the reference beam with a detector or an intensity of the combined beam with the detector; and
controlling the scanner such that an optical path of the measurement beam is changed to lead the measurement beam to the object in a case where the detected intensity of the reference beam is less than a threshold or not to lead the measurement beam to the object in a case where the detected intensity of the combined beam is higher than a threshold.

7. An image pickup apparatus for capturing an image of an object using optical coherence tomography, the image pickup apparatus comprising:
a scanner configured to scan the object with a measurement beam;
an optical system configured to irradiate the object with the measurement beam via the scanner and to form a combined beam by combining a reference beam and a return beam from the object irradiated with the measurement beam;
a detector configured to detect an intensity of the combined beam; and
a controller configured to control the scanner such that an optical path of the measurement beam is changed to not lead the measurement beam to the object in a case where the detected intensity of the combined beam is higher than a threshold.

8. The image pickup apparatus according to claim 7, wherein the controller is configured to reduce the intensity of the measurement beam for irradiating the object by changing a state in which the object is irradiated with the measurement beam to a state in which the object is not irradiated with the measurement beam in a case where the intensity of the combined beam detected by the detector exceeds the predetermined value.

9. The image pickup apparatus according to claim 7, wherein the controller is configured to reduce the intensity of the measurement beam for irradiating the object in a case where the intensity of the combined beam detected by the detector while the object is irradiated with the measurement beam is outside a predetermined range.

10. The image pickup apparatus according to claim 7, wherein the object is an eye, and
wherein, while the scanner scans the eye with the measurement beam, a retina of the eye is irradiated with the measurement beam via a cornea of the eye so that an image of the retina is captured.

11. An image pickup apparatus for capturing an image of an object comprising:
a scanner configured to scan the object with a measurement beam;
an optical system configured to irradiate the object with the measurement beam via the scanner and to form a combined beam by combining a reference beam and a return beam returned from the object irradiated with the measurement beam;
a detector configured to detect an intensity of a light intensity detection beam obtained by separating the reference beam; and
a controller configured to control the scanner such that an optical path of the measurement beam is changed to lead the measurement beam to the object in a case where the detected intensity of the light intensity detection beam is less than a threshold.

12. The image pickup apparatus according to claim 11, wherein the object is an eye, and
wherein, while the scanner scans the eye with the measurement beam, a retina of the eye is irradiated with the measurement beam via a cornea of the eye so that an image of the retina is captured.

13. The image pickup apparatus according to claim 11, wherein the controller is configured to reduce the intensity of the measurement beam for irradiating the object by changing a state in which the object is irradiated with the measurement beam to a state in which the object is not irradiated with the measurement beam in a case where the intensity of the detected light intensity detection beam does not satisfy a predetermined condition.

* * * * *